US012778887B2

(12) United States Patent
Anderson et al.

(10) Patent No.: US 12,778,887 B2
(45) Date of Patent: Nov. 3, 2026

(54) ALKALI METAL SALT COMBINATIONS OF INCOMPATIBLE ACTIVE PHARMACEUTICAL INGREDIENTS

(71) Applicant: HALEON US HOLDINGS LLC, Wilmington, DE (US)

(72) Inventors: Gary Bruce Anderson, Richmond, VA (US); Hope Patricia Bailey, Richmond, VA (US); Jonathon Michael Boggia, Richmond, VA (US); Kevin Scott Kinter, Richmond, VA (US); Rachel Elizabeth Moore, Richmond, VA (US); Jigna Dhanu Patel, Richmond, VA (US); Shivangi Akash Patel, Richmond, VA (US)

(73) Assignee: HALEON US HOLDINGS LLC, Wilmington, DE (US)

( * ) Notice: Subject to any disclaimer, the term of this patent is extended or adjusted under 35 U.S.C. 154(b) by 256 days.

(21) Appl. No.: 18/552,975

(22) PCT Filed: Apr. 27, 2022

(86) PCT No.: PCT/US2022/026443

§ 371 (c)(1),
(2) Date: Sep. 28, 2023

(87) PCT Pub. No.: WO2022/232211

PCT Pub. Date: Nov. 3, 2022

(65) Prior Publication Data

US 2025/0345274 A1 Nov. 13, 2025

Related U.S. Application Data

(60) Provisional application No. 63/180,784, filed on Apr. 28, 2021.

(51) Int. Cl.

| | |
|---|---|
| ***A61K 9/08*** | (2006.01) |
| ***A61K 9/48*** | (2006.01) |
| ***A61K 31/167*** | (2006.01) |
| ***A61K 31/192*** | (2006.01) |

(52) U.S. Cl.

CPC .............. *A61K 9/08* (2013.01); *A61K 9/4808* (2013.01); *A61K 9/485* (2013.01); *A61K 9/4858* (2013.01); *A61K 9/4866* (2013.01); *A61K 31/167* (2013.01); *A61K 31/192* (2013.01)

(58) Field of Classification Search

None

See application file for complete search history.

(56) References Cited

U.S. PATENT DOCUMENTS 5,071,643 A 12/1991 Yu et al.

FOREIGN PATENT DOCUMENTS

| | | | | |
|---|---|---|---|---|
| CN | 1483403 | A | * | 3/2004 |
| CN | 101816643 | A | * | 9/2010 |
| CN | 106794163 | A | | 5/2017 |
| WO | 88/02625 | A1 | | 4/1988 |
| WO | WO 1988002625 | | * | 4/1988 |
| WO | 20050063219 | A2 | | 7/2005 |

OTHER PUBLICATIONS

Gullapalli et al. "Soft gelatin capsules (softgels)" 2010.*

Preksha, P. et al. RP-HPLC Method Development and Validation for Simultaneous Estimation of Paracetamol and Ibuprofen in Soft Gelatin Capsule. Inventi Rapid: Pharm Analysis & Quality Assurance. vol. 3, 2014.

First Office Action in Chinese Application No. 202280031579.0; received on Jan. 23, 2026.

Park, H. J. et al., "Lidocaine-Ibuprofen Ionic Liquid for Dermal Anesthesia", AIChE Journal, 2015, vol. 61(9), pp. 2732-2738.

Chantereau, G. et al., "Design of Nonsteroidal Anti-Inflammatory Drug-Based Ionic Liquids with Improved Water Solubility and Drug Delivery", ACS Sustainable Chemistry & Engineering, 2019, pp. 14126-14134.

Jesus, A. R. et al., "Enhancement of water solubility of poorly water-soluble drugs by new biocompatible N-acetyl amino acid N-alkyl cholinium-based ionic liquids", Eur J Pharm Biopharm., 2019, vol. 137, pp. 227-232.

International Search Report and Written Opinion of International Application No. PCT/US2022/026443 mailed Aug. 8, 2022.

* cited by examiner

*Primary Examiner* — Danah Al-Awadi

(57) ABSTRACT

A composition comprises an alkali metal salt of a first pharmaceutical ingredient; and a second pharmaceutical ingredient, wherein the second pharmaceutical ingredient is chemically incompatible with the first pharmaceutical ingredient, and the composition is an aqueous solution. The first active pharmaceutical ingredient can comprise ibuprofen or naproxen. The second pharmaceutical ingredient can comprise acetaminophen.

11 Claims, 4 Drawing Sheets

ALKALI METAL SALT COMBINATIONS OF INCOMPATIBLE ACTIVE PHARMACEUTICAL INGREDIENTS

CROSS-REFERENCE TO RELATED APPLICATIONS

This application is a U.S. National Phase Application under 35 U.S.C. § 371 of International Application PCT/US2022/026443, filed on Apr. 27, 2022, which claims the benefit of priority to U.S. Provisional Patent Application 63/180,784, filed on Apr. 28, 2021, both of which are incorporated herein by reference in their entireties.

TECHNICAL FIELD

The invention is generally related to combinations of incompatible active pharmaceutical ingredients, and, more specifically, to liquid-stable combinations of incompatible active pharmaceutical ingredients.

BACKGROUND

Softgel capsules are popular with consumers, because the capsules offer an elegant dosage unit, and the liquid fill generally exhibits a fast dispersal of active pharmaceutical ingredients (API) relative to that of a compressed tablet. However, the many positives of softgels are often counter balanced with formulation challenges, particularly stability and solubility issues. Unfortunately, these issues can take months before they manifest in the softgel and are often the leading cause of softgel project failure. Consequently, although softgels are a highly desired dosage form from both the consumer and formulation perspective, it is a very challenging dosage form to develop.

Compositions, methods, and system that can overcome one or more of the stability and solubility issues associated with liquid fills is needed.

SUMMARY

In one aspect, a composition comprises an alkali metal salt of a first active pharmaceutical ingredient; and a second active pharmaceutical ingredient. In another aspect, a composition comprises an alkali metal salt of a first pharmaceutical ingredient; and a second pharmaceutical ingredient, wherein the second pharmaceutical ingredient is chemically incompatible with the first pharmaceutical ingredient, and the composition is an aqueous solution. The alkali metal can be sodium, potassium, or a combination of both. In some embodiments, at least 40%, at least 50%, at least 60%, at least 70%, at least 80%, at least 90% or 100% of the first active pharmaceutical ingredient is the alkali metal salt. In some cases, 40%-100% of the first active pharmaceutical ingredient is the alkali metal salt. When less than 100% of the first active pharmaceutical ingredient is ionized, the balance of the first active pharmaceutical ingredient is non-ionized.

The first active pharmaceutical ingredient can comprise ibuprofen, naproxen, ketoprofen, dexibuprofen, fenoprofen, dexketoprofen, flurbiprofen, oxaprozin, loxoprofen, diflunisal, etodolac, indomethacin, ketorolac, oxaprozin, piroxicam, salsalate, salicylic acid, indomethacin, tolmetin, sulindac, etodolac, ketordolac, diclofenac, aceclofenac, bromfenac, pharmaceutically acceptable salts thereof, or any combination thereof. In some preferred embodiments, the first active pharmaceutical ingredient comprises ibuprofen or naproxen.

Exemplary second active pharmaceutical ingredients comprise acetaminophen, phenylephrine, chlorpheniramine and dextromethorphan, cetirizine, pseudoephedrine, brompheniramine, guaifenesin, doxylamine, or any combination thereof.

In some instances, the composition comprises acetaminophen (paracetamol/APAP) and an alkali metal ibuprofen salt. A ratio of acetaminophen to the alkali metal ibuprofen salt can be 2:1 by weight in some embodiments. In some cases, the composition comprises 250 mg acetaminophen and alkali metal ibuprofen salt as the molar equivalent of 125 mg of ibuprofen free acid.

The composition can further comprise polyethylene glycol (PEG), methoxy-PEG (mPEG), derivatives thereof, and/or any combination thereof. In some cases, when present, PEG is PEG-200 to 1500.

In another aspect, a softgel capsule comprises a fill comprising a composition described herein.

A method of making an alkali metal salt of the first active pharmaceutical ingredient of the composition comprises mixing the first active pharmaceutical ingredient with sodium hydroxide, potassium hydroxide, or both in a solvent. In some embodiments, the method can further comprise adding an alkali metal hydroxide to a solution containing the first active pharmaceutical ingredient and the second active pharmaceutical ingredient to form the alkali metal salt of the active pharmaceutical in situ. In other embodiments, the method can comprise adding an alkali metal hydroxide to a solution containing the first active pharmaceutical ingredient to form the alkali metal salt of the active pharmaceutical ingredient; and adding the alkali metal salt of the active pharmaceutical ingredient to a solution comprising the second active pharmaceutical ingredient.

DETAILED DESCRIPTION

Figure 1:
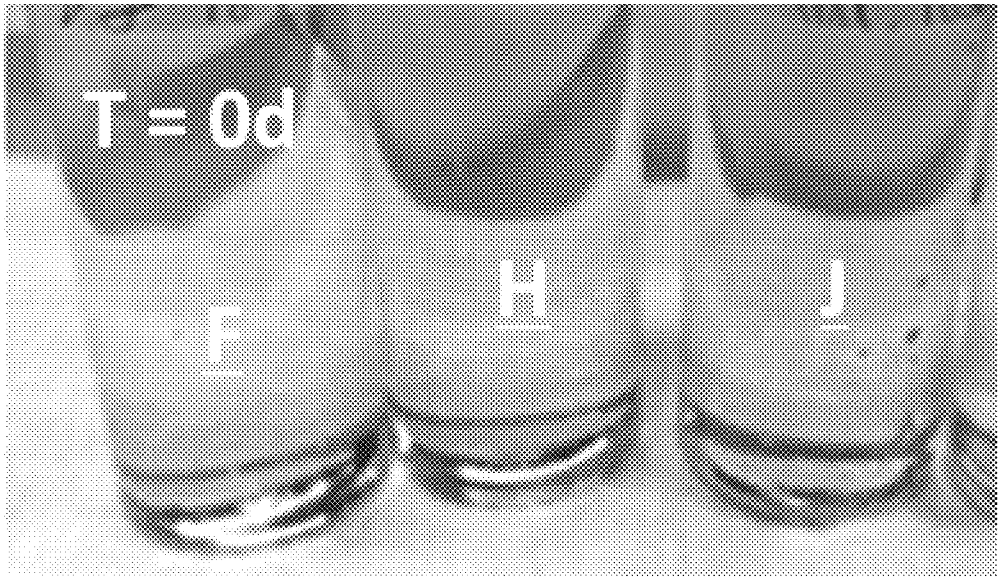
FIG. 1 is a photograph of vials having mixtures ibuprofen and acetaminophen in solution at T=0 days.

Embodiments described herein can be understood more readily by reference to the following detailed description, examples, and figures. Elements, apparatus, and methods described herein, however, are not limited to the specific embodiments presented in the detailed description, examples, and figures. It should be recognized that the exemplary embodiments herein are merely illustrative of the principles of the present invention. Numerous modifications and adaptations will be readily apparent to those of skill in the art without departing from the spirit and scope of the invention.

In addition, all ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9.

All ranges disclosed herein are also to be considered to include the end points of the range, unless expressly stated otherwise. For example, a range of "between 5 and 10" or "5 to 10" or "5-10" should generally be considered to include the end points 5 and 10.

It is further to be understood that the feature or features of one embodiment may generally be applied to other embodiments, even though not specifically described or illustrated in such other embodiments, unless expressly prohibited by this disclosure or the nature of the relevant embodiments. Likewise, compositions and methods described herein can include any combination of features and/or steps described herein not inconsistent with the objectives of the present disclosure. Numerous modifications and/or adaptations of the compositions and methods described herein will be readily apparent to those skilled in the art without departing from the present subject matter.

A principle point of complexity for liquid-filled softgels is that the liquid fill itself is often more problematic than tablet formulations. Liquid fills tend to have higher API degradation rates because the API(s) is in solution. When an incompatible or reactive species is present with the API in solution, degradation of the API is observed in contrast to solid state tablet formulations that can often separate these incompatible components. An example of this is ibuprofen (IBU). One of the major issues with IBU-containing softgel liquid fills is the formation of IBU esters with polyethylene glycol (PEG, hydrophilic softgel carrier), glycerin (gelatin plasticizer), sorbitol (gelatin plasticizer), and/or other common softgel components that have a reactive alcohol or carboxylic acid group, including API's having these functional groups (e.g. such as a non-steroidal anti-inflammatory drug ("NSAID") carboxylic acid group). Without being bound to theory, it is believed that the alcohol portions (R—OH) of both the PEG and sorbitol react with the IBU carboxylic acid moiety to form an ester. This lowers API levels and can cause IBU levels to fall out of specification. It is believed that this is the main degradation pathway of IBU in softgels. Such degradation pathways are also observed in other similar acetic acid and propionic acid-based APIs, such as naproxen, ketoprofen, and the like, further examples of which are described in more detail herein. Adjustments to the pH can aid in the solubility of the API but can also aid in the degradant formation of the APIs, further complicating the issue.

In addition to API reactivity/degradation issues observed in liquid fills, many API's also exhibit solubility challenges. For example, acetaminophen (APAP) demonstrates both solubility and reactivity/degradation challenges. APAP's solubility is largely independent of pH, having a solubility of approximately 20 mg/ml at 37° C. in water and across the pH range (~1-9) which most softgel liquid fills are formulated. However, a 20 mg/ml solubility rate is generally unsuitable for a high-dose API (where 250-500 mg is a typical dose), because the resulting softgel capsule size or quantity of softgel capsules needed to achieve the dose would be impractical for oral delivery. For instance, the size of the softgel capsule needed for a single dose would be so large as to be challenging or dangerous for a user to swallow. Conventional solutions to this problem often involve the use of co-solvents (like PEG) to increase APAP solubility enough to enable reasonably sized softgels. For example, APAPs solubility can be increased up to 260 mg/ml in an 80% PEG 400/water mixture. This increase in APAP solubility enables APAP to be formulated into a softgel, but this solubility improvement comes with a large penalty—the higher solubility leads to the second APAP formulation challenge-chemical stability.

While not intending to be bound by theory, it is believed that the principle degradation product of acetaminophen is hydrolysis of the APAP amide to 4-aminophenol (4-AP), which can lead to a variety of oxidative and other polymeric byproducts. These degradants cause a deep brown discoloration of the product. Hydrolysis of the amide of APAP to 4-aminophenol (4-AP) is accelerated at both acidic and basic conditions, with the lowest hydrolysis levels of APAP being observed in liquids with a pH between 5-6.

While a pH range of 5-6 may in some instances be acceptable for liquid fills that only have APAP present as an API, such conditions are problematic if APAP is combined with other API's, such as IBU. For example, liquids with a pH of 5-6 are generally too low for IBU to remain solubilized. Instead, IBU requires a higher (more basic) pH to be fully solubilized. Additionally, the free acid of IBU has been observed to accelerate degradation of APAP to 4-AP. Consequently, there is a tight balance that needs to be achieved between pH, water content, and the reactivities of IBU and APAP to successfully develop a combination softgel product. Seemingly minor modifications of any one of these physical parameters can dramatically affect stability.

In summary, although softgels are a highly desired dosage form from both the consumer and formulation perspective, softgel liquid fills can be a very challenging and unpredictable dosage form to develop.

As described in more detail herein, novel liquid fill compositions and methods for preparing liquid fill compositions are disclosed that address stability and/or solubility issues for API's. Specifically, one aspect described herein focuses on stabilizing solutions having traditionally incompatible API mixtures through ionization of one or more of the API's using alkali metal salts. As discussed, ionization of one or more of the API's can lead to increased stability for solutions having chemically incompatible API mixtures.

It is to be noted that while the principle focus of this disclosure is on softgel liquid fills, the described compositions and methods are not limited solely to this field. Instead, the skilled artisan would appreciate that such compositions and methods can be used in liquid oral or injectable compositions, or even in compositions and methods of preparing API's for solid dosage forms, such as for tablets, caplets, and the like.

I. COMPOSITIONS: ALKALI METAL SALTS OF ACTIVE PHARMACEUTICAL AGENTS

It has been discovered that ionization of a first active pharmaceutical ingredient ("API-1) with an alkali metal salt can also impart stability in solutions of otherwise incompatible active pharmaceutical ingredients. For example, stability has been discovered to increase in solutions having a combination of an alkali metal salt of a first active pharmaceutical ingredient and a chemically incompatible second active pharmaceutical ingredient (API-2). As described in more detail herein, it has surprisingly been discovered that when the first active pharmaceutical ingredient is in an alkali metal salt form, stability with otherwise incompatible second active pharmaceutical ingredients is observed and maintained in solution, even when less than 100% of the first active pharmaceutical ingredient is ionized.

In an aspect, a composition comprises an alkali metal salt of a first pharmaceutical ingredient ("API-1") and a chemically incompatible second pharmaceutical ingredient ("API-2"). Exemplary API-1's can comprise at least one or more than one acidic proton. For example, in some cases, API-1 has one or more protons with a pKa of 6.9 or less, 6.8 or less, 6.6 or less, 6.4 or less, 6.2 or less, 6.0 or less, 5.8 or less, 5.6 or less, 5.4 or less, 5.2 or less, 5.0 or less, 4.8 or less, 4.6 or less, 4.4 or less, 4.2 or less, 4.0 or less, 3.5 or less, or 3.0 or less. Any API having an acidic proton described herein not inconsistent with the objectives of this disclosure is generally contemplated. Exemplary functional groups having an acidic proton include, but are not limited to, carboxylic acids, hydroxyls, phenols, sulfonamides, sulfonylureas, β-dicarbonyl compounds, and the like. In a preferred embodiment, API-1 comprises a carboxylic acid and/or phenol.

In some embodiments, API-1 comprises a propionic acid-based non-steroidal anti-inflammatory drug (NSAID). In some instances, API-1 comprises an acetic acid-based NSAID. Exemplary API-1 include ibuprofen, naproxen, ketoprofen, dexibuprofen, fenoprofen, dexketoprofen, flurbiprofen, oxaprozin, loxoprofen, diflunisal, etodolac, indomethacin, ketorolac, oxaprozin, piroxicam, salsalate, sulindac, sulindac, salicylic acid, indomethacin, tolmetin, sulindac, etodolac, ketordolac, diclofenac, aceclofenac, bromfenac, pharmaceutically acceptable salts thereof, or any combination thereof. In preferred embodiments, API-1 comprises ibuprofen or naproxen.

The term "alkali metal" is understood to include sodium, potassium, or a combination of both. Thus, the ionized form of API-1 would be the corresponding sodium or potassium salt.

In some embodiments, at least 40%, at least 50%, at least 60%, at least 70%, at least 80%, at least 90% or 100% of API-1 is present as an alkali metal salt. In some cases, 40-100%, 40-95%, 40-90%, 40-85%, 40-80%, 40-75%, 40-70%, 40-65%, 40-60%, 40-55%, 40-50%, 45-95%, 50-95%, 55-95%, 60-95%, 65-95%, 70-95%, 75-95%, 80-95%, 90-95%, 45-85%, 50-80%, 55-75%, 60-70%, 40%, 45%, 50%, 55%, 60%, 65%, 70%, 75%, 80%, 85%, 90%, or 95% of the first active pharmaceutical ingredient is ionized as an alkali metal salt. In embodiments where the ionization level of the API-1 salt is less than 100%, the balance of API-1 present in the composition is a non-ionized form of the API-1, where the % is a % mol/mol. For instance, if 80% of API-1 in a composition is an alkali metal ibuprofen salt, the 20% remaining balance of API-1 is the free acid form of ibuprofen.

The degree of API-1 ionization can be selected for a desired physical property of the composition. For example, in some cases, the degree of API-1 ionization can adversely or positively affect chemical compatibility of API-1 with other API's present in the composition (such as a chemically incompatible API-2); chemical compatibility with excipients present in the composition; chemical compatibility of the composition with encapsulating material in instances when the composition is a softgel fill; solubility of API-1 itself in the composition; and other similar instances. Notably, as described herein in more detail in the EXAMPLES, the chemical compatibility of different API-1 ionization levels with other ingredients or components is often highly unpredictable, specific to the particular API being used, and often desirable chemical compatibility with one ingredient or component of the composition results in undesirable chemical incompatibility with another ingredient or component of the composition. For example, in some instances, lower degrees of API-1 ionization can improve compatibility of the composition with a softgel gelatin capsule in some instances, but simultaneously reduce the solubility of another API present (such as API-2) in the composition and/or reduce the chemical compatibility between API-1 and API-2. For instance, it has been observed herein that ionization levels of sodium/potassium ibuprofen salts below approximately 40% result in the ibuprofen free acid being insoluble in the composition when the composition comprises polyethylene glycol (PEG).

The chemically incompatible second active pharmaceutical ingredient (API-2) can be any active pharmaceutical ingredient not inconsistent with the objectives of this disclosure. In some instances, suitable API-2 include analgesics, anti-inflammatory agents, antacids, anti-bacterial agents, anti-coagulants, anti-diarrheals, anti-fungals, anti-migraine agents, anti-muscarinic agents, anti-protazoal agents, corticosteroids, cough suppressants, decongestants, diuretics, enzymes, gastro-intestinal agents, histamine receptor antagonists, laxatives, local anesthetics, nutritional agents, purgatives, stimulants, and any combination thereof.

In preferred embodiments, API-2 comprises acetaminophen, phenylephrine, chlorpheniramine and dextromethorphan, cetirizine, pseudoephedrine, brompheniramine, guaifenesin, doxylamine, methocarbamol, diphenhydramine, melatonin, valerian, or any combination thereof. In a preferred embodiment, API-2 is acetaminophen (APAP).

The term "chemically incompatible" means that API-1 and/or API-2 typically degrade when present in solution with each other. For example, as described in Example 1, when IBU is combined with APAP in solution, APAP is observed to degrade through at least acid catalysis by IBU.

The combination of the API-1 alkali metal salt and the chemically incompatible API-2 provides a number of beneficial and unexpected results over non-ionized API-1's. For example, in many cases the API-1 alkali metal salt acts as a solubilizing agent for API-2, allow for greater concentrations of API-2 to be obtained when used in combination with the API-1 alkali metal salt. Even more unexpectedly, in many cases, this solubility enhancement effect was observed for API-1 alkali metal salts that were less than 100% ionized. For example, solubility enhancement for compositions herein were observed for API-1 alkali metal salt levels being between 40-100% ionized. Levels below 40% ionization generally resulted in API-1 and/or API-2 crystalizing and not remaining solubilized, such as when API-1 is ibuprofen and API-2 is acetaminophen. However, in some cases API-1 and/or API-2 may remain solubilized with ionization levels as low as 25%, as low as 30%, or as low as 35%, with these lower levels being dependent upon the specific API-1 and/or API-2.

An additional surprising result is that reactivity of API-1 is reduced when in the alkali metal salt form, allowing stable combinations of the alkali metal API-1 salt and API-2 to be created in liquid forms in contrast to the un-ionized API-1 and API-2 combination that degrades under the same conditions. While not intending to be bound by theory, it is believed that the positively charged alkali metal (such as sodium or potassium) interacts with a negatively charged group of API-1 (such as a negatively charged carboxylic acid of IBU) to form an alkali metal complex therebetween. This alkali metal API-1 salt reduces the reactivity of the negatively charged group of API-1, permitting stable, liquid combinations of incompatible API's to be prepared.

For example, as previously discussed herein and shown in the EXAMPLES below, conventional liquid compositions of IBU and APAP rapidly display severe discoloration from degradation of APAP to 4-aminophenol. In some embodiments, compositions herein comprise stable liquid combinations of alkali metal salts of IBU and APAP. In some cases, compositions described herein of alkali metal salts of IBU and APAP exhibit stability after 24-36 months at room temperature.

Figure 5:
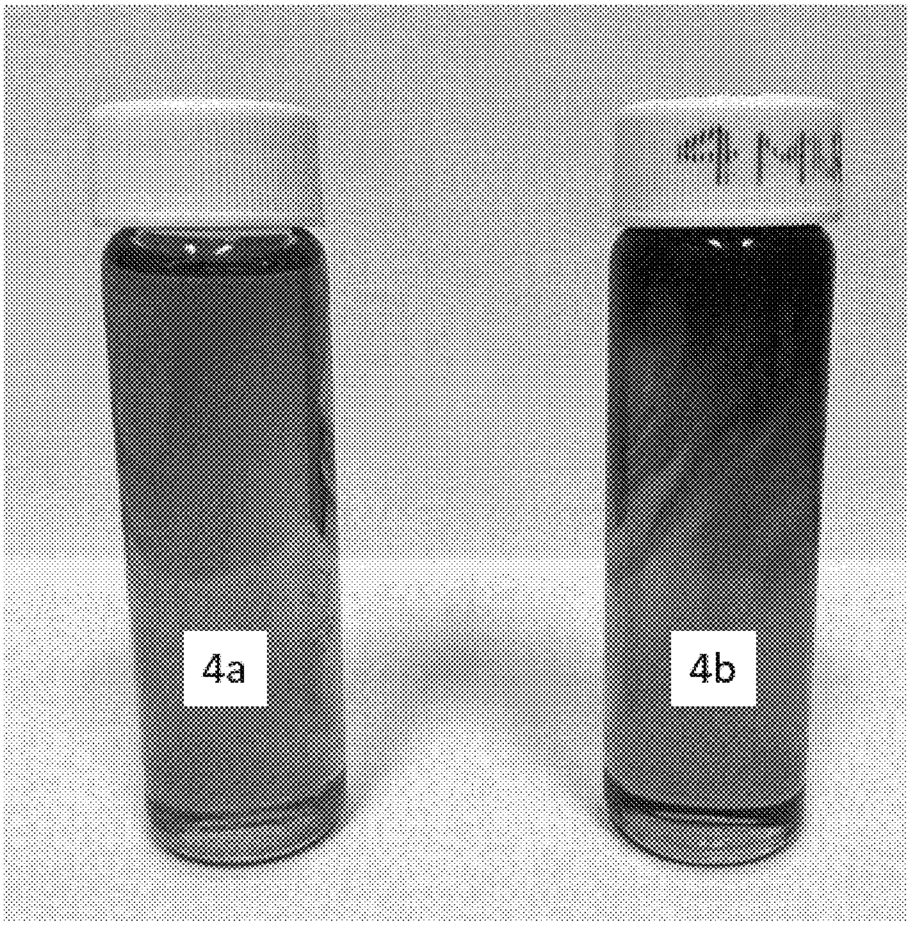
FIG. 5 is a photograph of two vials having a solution of 48.5% ionized sodium naproxen and acetaminophen in PEG-400, with one being at ambient temperature and humidity and the other at 40° C. and 75% humidity after 7 days.

Similarly, liquid compositions of naproxen and APAP also display discoloration from degradation of the two API's in a similar manner to that of IBU and APAP, as seen for instance in FIG. 5 and discussed in more detail in Example 4. Thus, in some embodiments described herein, compositions herein comprise stable liquid combinations of alkali metal naproxen salts and APAP.

In some specific embodiments, a composition described herein comprises 50-250 mg acetaminophen and 125-500 mg alkali metal ibuprofen salts. In some cases, acetaminophen is present in the composition in an amount of 60-225 mg, 75-200 mg, 100-175 mg, 125-150 mg, 50 mg, 60 mg, 75 mg, 100 mg, 125 mg, 150 mg, 175 mg, 200 mg, 225 mg, or 250 mg. Alkali metal Ibuprofen salts can be present in this embodiment comprising 125-450 mg, 125-400 mg, 125-350 mg, 125-325 mg, 125-300 mg, 125-275 mg, 125-250 mg, 125-225 mg, 125-200 mg, 125-150 mg, 150-500 mg, 175-500 mg, 200-500 mg, 225-500 mg, 250-500 mg, 275-500 mg, 300-500 mg, 325-500 mg, 350-500 mg, 375-500 mg, 400-500 mg, 425-500 mg, 450-500 mg, 125 mg, 150 mg, 175 mg, 200 mg, 225 mg, 250 mg, 275 mg, 300 mg, 325 mg, 350 mg, 375 mg, 400 mg, 425 mg, 450 mg, or 500 mg.

In some cases, the ratio of API-2 to alkali metal API-1 salt in a composition is 1:0.05, 1:0.12, 1:0.25, 1:0.5, 1:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, 10:1, or greater than 10:1. In some embodiments, API-2 is APAP and API-1 is a sodium and/or potassium IBU salt, and a ratio of API-2 to API-1 is 2:1 by weight.

As previously mentioned, in some embodiments, compositions described herein can further comprise a polyethylene glycol (PEG) and/or derivatives thereof, such as alkylated derivatives including methoxylated PEGs (mPEG). In some instances, PEG has an average molecular weight of 200-1500, 200-1450, 200-1400, 200-1350, 200-1300, 200-1250, 200-1200, 200-1150, 200-1100, 200-1050, 200-1000, 200-950, 200-900, 200-850, 200-800, 200-750, 200-700, 200-650, 200-600, 200-550, 200-500, 200-450, 200-400, 200-350, 200-300, 200-250, 250-1500, 300-1500, 350-1500, 400-1500, 450-1500, 500-1500, 550-1500, 600-1500, 650-1500, 700-1500, 750-1500, 800-1500, 850-1500, 900-1500, 950-1500, 1000-1500, 1050-1500, 1100-1500, 1150-1500, 1200-1500, 1250-1500, 1300-1500, 1350-1500, 1400-1500, 250-1450, 300-1400, 350-1350, 400-1300, 450-1250, 500-1200, 550-1150, 600-1100, 650-1050, 700-1000, 750-950, 800-900, 200, 250, 300, 350, 400, 450, 500, 550, 600, 650, 700, 750, 800, 850, 900, 950, 1000, 1050, 1100, 1150, 1200, 1250, 1300, 1350, 1400, 1450, or 1500.

In some embodiments, compositions described herein comprise PEG to API ratios of 0.5 to 2.5, 0.6 to 2.5, 0.7 to 2.5, 0.8 to 2.5, 0.9 to 2.5, 1.0 to 2.5, 1.1 to 2.5, 1.2 to 2.5, 1.3 to 2.5, 1.4 to 2.5, 1.5 to 2.5, 1.6 to 2.5, 1.7 to 2.5, 1.8 to 2.5, 1.9 to 2.5, 2.0 to 2.5, 2.1 to 2.5, 2.2 to 2.5, 2.3 to 2.5, 1.0 to 2.4, 1.0 to 2.3, 1.0 to 2.2, 1.0 to 2.1, 1.0 to 2.0, 1.0 to 1.9, 1.0 to 1.8, 1.0 to 1.7, 1.0 to 1.6, 1.0 to 1.5, 1.0 to 1.4, 1.0 to 1.3, 1.0 to 1.2, 1.1 to 2.4, 1.1 to 2.1, 1.2 to 2.3, 1.3 to 2.2, 1.4 to 2.1, 1.5 to 2.0, 1.6 to 1.9, 0.5 to 1.5, 0.6 to 1.4, 0.7 to 1.3, 0.8 to 1.2, or 0.9 to 1.1. It is to be noted that these PEG to API ratios are merely exemplary and are dependent on the API dose. For example, the disclosed ratios could apply in situations where the API is IBU, APAP, or a combination of both, which are typically considered to be high dose API's. In low dose API example, the ratios can be much higher, such as 1.0 to 5.0, 1.0-10.0, 1.0-15.0, 1.0 to 20.0, 1.0 to 30.0, 1.0 to 40.0, 1.0 to 50.0, 1.0 to 60.0, 1.0 to 70.0, 1.0 to 80.0, 1.0 to 90.0, 1.0 to 100.0, 1.0 to 150.0, 1.0 to 200.0, or 1.0 to 500.0, 1.0 to 1000.0, or even higher, such as 1.0 to 10,000.0.

In some embodiments, compositions described herein can further comprise water. Water can be present in the composition between 0.5-15 wt. %, 0.5-14 wt. %, 0.5-13 wt. %, 0.5-12 wt. %, 0.5 to 11 wt. %, 0.5-10 wt. %, 0.5-9 wt. %, 0.5-8 wt. %, 0.5-7 wt. %, 0.5-6 wt. %, 0.5-5 wt. %, 0.5-5 wt. %, 0.5-4 wt. %, 0.5-3 wt. %, 0.5-2 wt. %, 0.5-1 wt. %, 10 wt. %, 9 wt. %, 8 wt. %, 7 wt. %, 6 wt. %, 5 wt. %, 4 wt. %, 3 wt. %, 2 wt. %, 1 wt. %, up to 15 wt. %, up to 13 wt. %, up to 10 wt. %, up to 5 wt. %, up to 4 wt. %, up to 3 wt. %, up to 2 wt. %, up to 1 wt. %, or up to 0.5 wt. %. In some cases, water is present when the final composition is a liquid, such as when the composition is a softgel liquid fill. However, in other cases, water can be present during preparation of the composition, but absent or less than 10 wt. %, less than 5 wt. %, less than 4 wt. %, less than 3 wt. %, less than 2 wt. %, less than 1 wt. %, or less than 0.5 wt. % in the final composition when the final composition is a solid, such as when the final composition is used in a solid product (e.g. compressed tablet).

Compositions described herein can optionally further comprise one or more excipients, such as a solubility enhancer, a surfactant, a structure former, a cosolvent, inorganic salts, a coloring agent, and/or a viscosity enhancer. In cases where the composition is a solid, the composition can optionally comprise or further comprise a starch, a preservative, an antioxidant, a flavoring agent, a pH modifier, a sweetener, or any combination thereof.

Solubility enhancers include glycerin, polyvinylpyrrolidone, propylene glycol, cyclodextrins, ethylene glycols, or any combination thereof, including common chemical derivatives known to those skilled in the art. Solubility enhancers can be present between 1-15 wt. %, 2-14 wt. %, 3-13 wt. %, 4-12 wt. %, 5-11 wt. %, 6-10 wt. %, 7-9 wt. %, 1-14 wt. %, 1-13 wt. %, 1-12 wt. %, 1-11 wt. %, 1-10 wt. %, 1-9 wt. %, 1-8 wt. %, 1-7 wt. %, 1-6 wt. %, 1-5 wt. %, 1-4 wt. %, 1-3 wt. %, 2-15 wt. %, 3-15 wt. %, 4-15 wt. %, 5-15 wt. %, 6-15 wt. %, 7-15 wt. %, 8-15 wt. %, 9-15 wt. %, 10-15 wt. %, 11-15 wt. %, 12-15 wt. %, 13-15 wt. %, 5-9 wt. %, or 4-8 wt.

Surfactants can be any type known to those of ordinary skill in the art, so long as the surfactant is not inconsistent with the objectives of this disclosure. Exemplary surfactants include sodium lauryl sulfate, sodium laureth sulfate, ammonium lauryl sulfate, sodium stearate, potassium cocoate, and any combination thereof. When present in the composition, surfactants can be present in any amount not inconsistent with the objectives of this disclosure.

Structure formers can include a polyol, such as mannitol, dextrose, lactose, galactose, glycine, galactose, glycine, cyclodextrin, or combinations thereof. In some embodiments, the structure former can be present in the composition in an amount of 0.1-5.0 wt. %, 0.1-4.8 wt. %, 0.1-4.6 wt. %, 0.1-4.4 wt. %, 0.1-4.2 wt. %, 0.1-4.0 wt. %, 0.1-3.8 wt. %, 0.1-3.6 wt. %, 0.1-3.4 wt. %, 0.1-3.2 wt. %, 0.1-3.0 wt.

%, 0.1-2.8 wt. %, 0.1-2.6 wt. %, 0.1-2.4 wt. %, 0.1-2.2 wt. %, 0.1-2.0 wt. %, 0.1-1.8 wt. %, 0.1-1.6 wt. %, 0.1-1.4 wt. %, 0.1-1.2 wt. %, 0.1-1.0 wt. %, 0.1-0.8 wt. %, 0.1-0.6 wt. %, 0.1-0.4 wt. %, 0.1 wt. %, 0.5 wt. %, 0.8 wt. %, 1.0 wt. %, 1.5 wt. %, 2.0 wt. %, 2.5 wt. %, 3.0 wt. %, 3.5 wt. %, 4 wt. %, 4.5 wt. %, or 5.0 wt. %.

In preferred embodiments, compositions described herein comprise water as a solvent. However, in some instances, a cosolvent can additionally be present, such as an alcohol including ethanol, isopropanol, or tert-butyl alcohol glycerin, propylene glycol, polyethylene glycol (PEG), or any combination thereof. In some embodiments, the cosolvent is present in the composition in an amount of up to 5 wt. %, up to 4 wt. %, up to 3 wt. %, up to 2 wt. %, up to 1 wt. %, less than 1 wt. %, 0.5-5 wt. %, 0.5-4.5 wt. %, 0.5-4 wt. %, 0.5-3.5 wt. %, 0.5-3 wt. %, 0.5-2.5 wt. %, 0.5-2 wt. %, 0.5-1.5 wt. %, 0.5-1 wt. %, 1-5 wt. %, 2-5 wt. %, 3-5 wt. %, or 0.5-2 wt. %.

In some cases, inorganic salts can be present in the composition, such as chlorides (Na and K), aluminum silicates, carbonates (Mg, Ca, Li, Mn), bicarbonates (Mg, Ca, Li, Mn), or any combination thereof. Inorganic salts can be present by intentional addition or as byproducts of previous method steps used to prepare the composition. For example, in some cases when the API starting material is in a salt form, the inorganic salt biproduct can be present in equal mol. % to the final API mol. %.

The starch, preservative, antioxidant, and viscosity enhancer can be any such component known in the art that is not inconsistent with the objectives of this disclosure.

Exemplary coloring agents can include FD&C dyes, such as Blue No. 1 and 2, Green No. 3, Red No. 3 and 40, and Yellow No. 5 and 6, as well as various oxides, such as red, yellow, and black iron oxides, or any combination thereof.

While softgel liquid fill compositions generally do not include a flavoring agent, in embodiments where the composition is used in solid or liquid formulations (such as tablets, syrups, and the like), flavoring agents such as raspberry, cherry, grape, vanilla, mint, strawberry, orange, lemon, caramel, licorice, or any combination thereof can be used.

Exemplary pH modifiers can include sodium hydroxide, hydrochloric acid, citric acid, phosphoric acid, tartaric acid, maleic acid, hydroxides (Na or K), carbonates (Mg, Ca, Li, Mn), bicarbonates (Mg, Ca, Li, Mn), or any combination thereof.

Exemplary sweeteners can include sucrose, aspartame, sucralose, acesulfame K and thaumatin, or combinations thereof.

In some embodiments, compositions described herein are liquid formulas, such as syrups. In other embodiments, compositions described herein are a softgel capsule liquid fill. In yet other embodiments, compositions described herein are dry formulations.

II. METHODS: ALKALI METAL SALTS

In another aspect, a method of making an alkali metal salt of the first active pharmaceutical ingredient described in Section I herein comprises mixing the first active pharmaceutical ingredient with sodium hydroxide, potassium hydroxide, or both in a solvent.

In another embodiment, a method of making a composition described in Section I herein comprises adding an alkali metal hydroxide to a solution containing the first active pharmaceutical ingredient and the second active pharmaceutical ingredient to form the alkali metal salt of the active pharmaceutical in situ.

In yet another embodiment, a method of making a composition described in Section I herein comprises adding an alkali metal hydroxide to a solution containing the first active pharmaceutical ingredient to form the alkali metal salt of the active pharmaceutical ingredient; and adding the alkali metal salt of the active pharmaceutical ingredient to a solution comprising the second active pharmaceutical ingredient.

III. EMBODIMENTS

The skilled artisan would understand that modifications and variations of the compositions described herein can be made within the scope of the invention. The following exemplary embodiments illustrate some, but not all variations of the invention.

Embodiment 1. A composition comprising an alkali metal salt of a first pharmaceutical ingredient; and a second pharmaceutical ingredient.

Embodiment 2. The composition of Embodiment 1, wherein the second pharmaceutical ingredient is chemically incompatible with the first pharmaceutical ingredient.

Embodiment 3. The composition of Embodiments 1 or 2, wherein the composition is an aqueous solution.

Embodiment 4. The composition of any of the previous Embodiments, wherein the alkali metal is sodium, potassium, or a combination of both.

Embodiment 5. The composition of any of the previous Embodiments, wherein at least 40%, at least 50%, at least 60%, at least 70%, at least 80%, at least 90% or 100% of the first active pharmaceutical ingredient is the alkali metal salt.

Embodiment 6. The composition of Embodiment 5, wherein 40%-100% of the first active pharmaceutical ingredient is the alkali metal salt.

Embodiment 7. The composition of Embodiments 5 or 6, wherein the balance of the first active pharmaceutical ingredient is non-ionized.

Embodiment 8. The composition of any of the previous Embodiments, wherein the first active pharmaceutical ingredient comprises ibuprofen, naproxen, ketoprofen, dexibuprofen, fenoprofen, dexketoprofen, flurbiprofen, oxaprozin, loxoprofen, diflunisal, etodolac, indomethacin, ketorolac, oxaprozin, piroxicam, salsalate, salicylic acid, indomethacin, tolmetin, sulindac, etodolac, ketordolac, diclofenac, aceclofenac, bromfenac, pharmaceutically acceptable salts thereof, or any combination thereof.

Embodiment 9. The composition of any of the previous Embodiments, wherein the first active pharmaceutical ingredient comprises ibuprofen or naproxen.

Embodiment 10. The composition of any of the previous Embodiments, further comprising polyethylene glycol (PEG), methoxy-PEG (mPEG), derivatives thereof, and/or any combination thereof.

Embodiment 11. The composition of Embodiment 10, wherein PEG is PEG-200 to 1500.

Embodiment 12. The composition of any of the previous Embodiments, further comprising water.

Embodiment 13. The composition of any of the previous Embodiments, wherein the second active pharmaceutical ingredient comprises acetaminophen, phenylephrine, chlorpheniramine and dextromethorphan, cetirizine, pseudoephedrine, brompheniramine, guaifenesin, doxylamine, or any combination thereof.

Embodiment 14. A softgel capsule comprising a fill comprising the composition of any of the previous Embodiments.

Embodiment 15. A method of making an alkali metal salt of the first active pharmaceutical ingredient of any of Embodiments 1-13 comprising: mixing the first active pharmaceutical ingredient with sodium hydroxide, potassium hydroxide, or both in a solvent.

Embodiment 16. A method of making the composition of Embodiment 15, comprising: adding an alkali metal hydroxide to a solution containing the first active pharmaceutical ingredient and the second active pharmaceutical ingredient to form the alkali metal salt of the active pharmaceutical in situ.

Embodiment 17. A method of making the composition of Embodiment 15, comprising: adding an alkali metal hydroxide to a solution containing the first active pharmaceutical ingredient to form the alkali metal salt of the active pharmaceutical ingredient; and adding the alkali metal salt of the active pharmaceutical ingredient to a solution comprising the second active pharmaceutical ingredient.

Example 1

Ibuprofen and Acetaminophen Combination Degradation

Stability of ibuprofen and acetaminophen mixtures were tested over 21 days using pre-formulations described in Table 1, where chemical changes were identified by color changes to the pre-formulations. Each pre-formulation was generally made by mixing the listed components together while heating to 40°-70° C. until everything is dissolved. Specifically for APAP-containing pre-formulation D, PEG 400 was first combined with water. Then povidone K-12 was dissolved in PEG-400 while being heated at approximately 30°-40° C. The temperature of the resulting solution was then raised to 70° C. and APAP was added. The resulting suspension was stirred until APAP dissolved. For APAP-containing pre-formulation G, PEG 400 was heated to 70° C. before added APAP, and the resulting suspension was stirred until APAP dissolved.

TABLE 1

APAP/IBU FORMULATION STABILITY SCREEN COMPOSITIONS

| PRE-FORMULATION | COMPOSITION |
|---|---|
| A | PEG 400<br>POVIDONE K-12 (“PVP” OR “K-12”)<br>WATER |
| B | IBU<br>PEG-400<br>50% KOH*<br>WATER* |
| D | APAP<br>PEG-400<br>K-12<br>WATER |
| E | IBU<br>PEG-400<br>K-12 |
| G | APAP<br>PEG-400 |
| I | IBU<br>PEG-400 |
| K | APAP<br>SODIUM IBU<br>PEG-400 |

*ALL FORMULATIONS WERE PREPARED IN DUPLICATES AND WERE STORED WITH AND WITHOUT NITROGEN GAS PURGE. ALL SAMPLES THAT DEGRADED EXHIBITED SLOWER DEGRADATION WHEN NITROGEN GAS PURGED.

Additional pre-formulations L-O were prepared having a combination of APAP/IBU/PEG 400/K-12/Water/KOH in addition to one or more antioxidants, as shown in Table 2. Pre-formulations L-O were prepared by combining pre-formulations A and B to give a base formulation comprising 74 wt. % of pre-formulation B and 25 wt. % of pre-formulation A. Each antioxidant was added to the base formulation in the amount indicated in Table 2.

TABLE 2

APAP/IBU FORMULATION STABILITY SCREEN COMPOSITIONS WITH ANTIOXIDANTS

| PRE-FORMULATION | ANTIOXIDANT ADDITIVE |
|---|---|
| L | ETHYLENEDIAMINETETRAACETIC ACID (“EDTA”) |
| M | PROPYL GALLATE |
| N | SODIUM SULFITE |
| O | SODIUM SULFITE<br>EDTA |

To assess the stability of the pre-formulations, a 14-day stability study was conducted at −20° C. and 5° C., with chemical changes being identified based on color changes in the solution. After 14 days, all of the pre-formulations showed no precipitate or change in solution appearance, indicating that the pre-formulations are physically stable at low temperatures.

A second 14-day stability study was conducted for pre-formulations A-O at room temperature. In these studies, all pre-formulations containing a mixture of IBU and APAP turned amber after 2 weeks.

Accelerated stability studies were conducted on Formulations A-O over three weeks, the results of which are summarized in Table 3.

TABLE 3

ACCELERATED STABILITY STUDIES OF FORMULATIONS A-O AT 40° C.

| FORMULATION | COMPOSITION | COLOR CHANGE @ 40° C. |
|---|---|---|
| A | PEG400/K-12/WATER | NO |
| B | IBU/PEG400/KOH/WATER | NO |
| C | 75% A + 25% B | NO |
| D | APAP/PEG400/K-12 | NO |
| E | IBU/PEG400/K-12 | YES-GOLDEN YELLOW |
| F | 67% D + 33% E | YES-BROWN WITHIN 2 DAYS |
| G | APAP/PEG400 | NO, CLEAR FOR > 1 MONTH |
| H | 75% G + 25% B | YES-BROWN WITHIN 2 DAYS |
| I | IBU/PEG400 | NO, CLEAR |
| J | 75% G + 25% I | YES-BROWN WITHIN 2 DAYS |
| K | APAP/SODIUM IBU/PEG400 | YES-VERY SLIGHT PINK AFTER 1 WEEK |

TABLE 3-continued

| ANTI-OXIDANTS | APAP/IBU/PEG400/K-12/WATER/KOH | |
|---|---|---|
| L | 0.05% EDTA | YES* |
| M | 0.0125% PROPYL GALLATE | YES* |
| N | 0.025% SODIUM SULFITE | YES-AFTER 1 WEEK BROWNING ON TOP WITH NON-$N_2$ VIAL* |
| O | 0.025% SODIUM SULFITE + 0.0625% EDTA | YES*-AFTER 1 WEEK BROWNING ON TOP WITH NON-$N_2$ VIAL.* |

*FORMULATIONS WERE STORED WITH AND WITHOUT $N_2$ PURGE. ALL $N_2$ PURGED SAMPLES BROWNED SLOWER.

As summarized in Table 3, pre-formulations having IBU or APAP as the sole API visually remain stable, with little to no color changes observed. On minor exception to this observation is IBU formulations with PEG 400 and PVP (e.g. pre-formulation E). These pre-formulations were observed to turn a very faint yellow color initially, and a darker yellow when heated at 40° C. It is believed that the yellow color is from oxidation of PVP.

Figure 2:
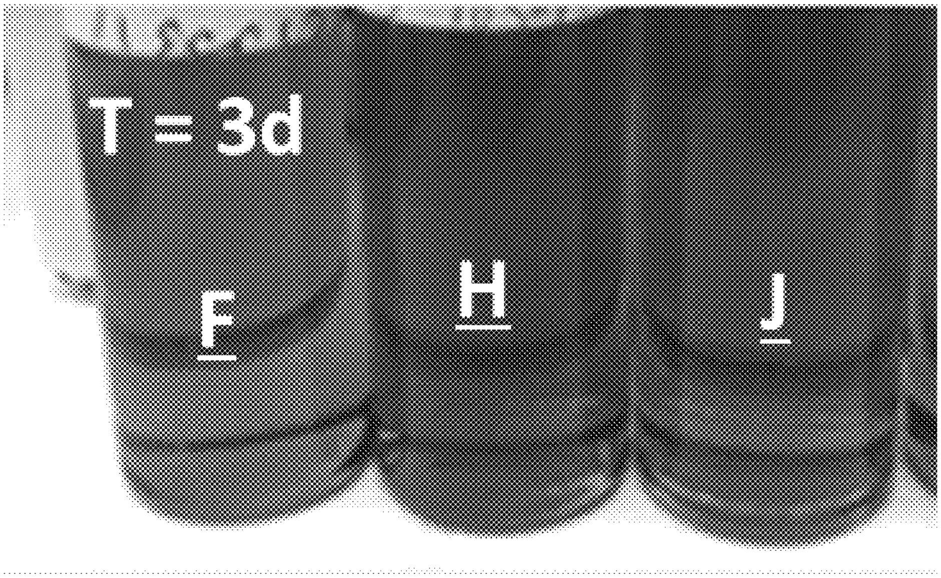
FIG. 2 is a photograph of the vials in FIG. 1 after T=3 days.
Figure 3:
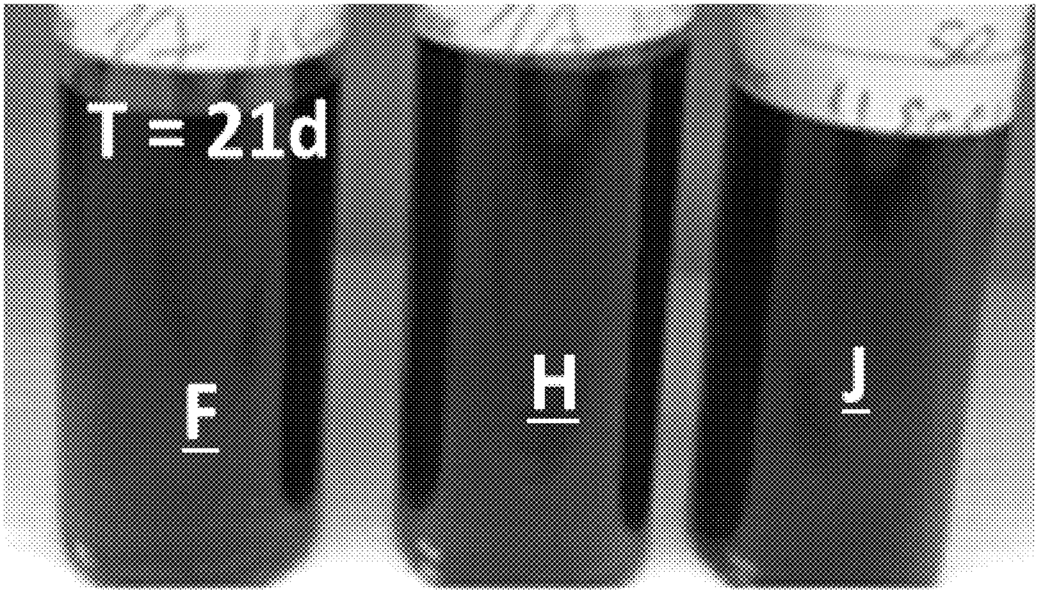
FIG. 3 is a photograph of the vials in FIGS. 1 and 2 after T=21 days.

Pre-formulations F, H, and J, each having different combinations of IBU+APAP in PEG 400, turned from clear to brown within a few days at an elevated temperature of 40° C. FIGS. 1-3 show the browning process for pre-formulations F (1), H (2), and J (3) at time (T)=0 days (clear) (FIG. 1), T=3 day (amber) (FIG. 2), and T=21 days (brown) (FIG. 3), respectively. Analytical HPLC/MS analysis of a random sampling of the pre-formulations revealed the presence of P-aminophenol degradants of APAP. Thus, the amber and dark brown color changes observed for these pre-formulations provided a visual indication of APAP degradation.

Figure 4A:
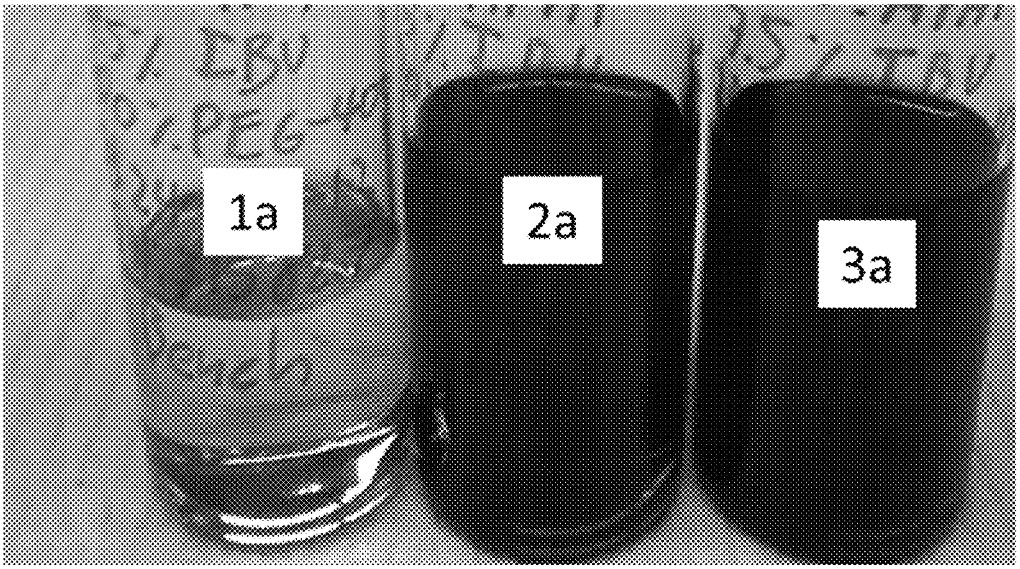
FIG. 4A is photograph of free acid ibuprofen and acetaminophen pre-formulation mixtures under various conditions and durations.
Figure 4B:
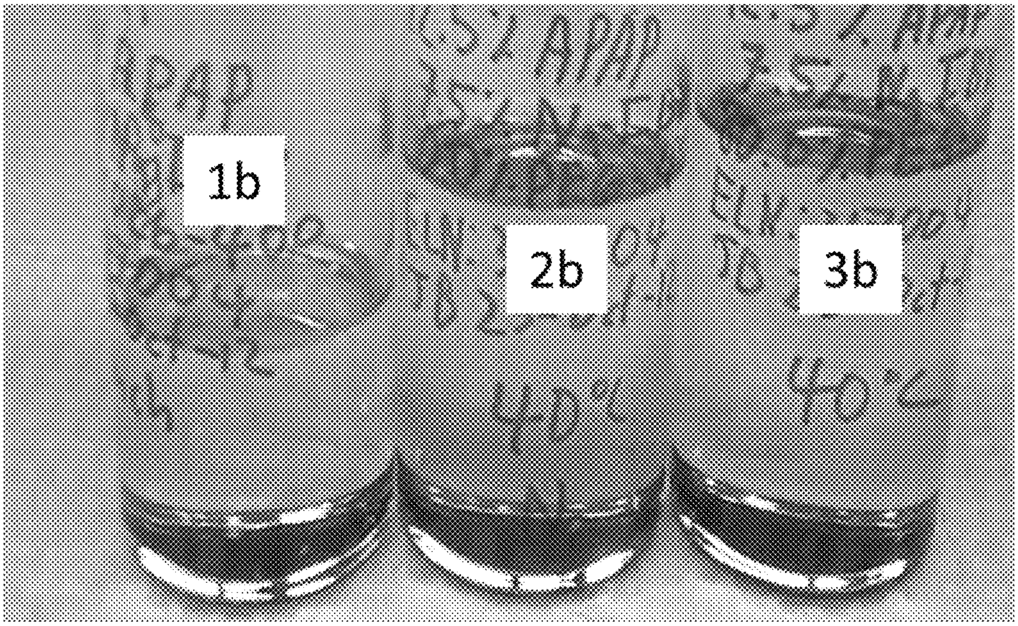
FIG. 4B is a photograph of sodium ibuprofen and acetaminophen pre-formulation mixtures under various condition and durations.

Pre-formulation K, which comprised 7.5 wt. % sodium IBU+12.5 wt. % APAP in 80 wt. % PEG 400, did not display the same color change from clear to brown as observed for IBU/APAP-containing pre-formulations F, H, and J. Instead, pre-formulation K remained clear, with only a lightly pinkish tint (and an apparent pH>8) when stored at both room temperature and at 40° C. for T=6, 7 and 21 days. As discussed in more detail in Example, 2, FIG. 4B shows sodium ibuprofen and APAP pre-formulation K mixtures under various condition and durations, with little to no color changes. Pre-formulation K is discussed in more detail in Example 2 herein.

Pre-formulations L-O explored the effects of various antioxidants as possible additives that could reduce or eliminate the oxidative degradation of APAP in pre-formulations B+D (APAP/IBU/PEG 400/K-12/water/KOH). As shown in Table 3, the presence of EDTA, propyl gallate, sodium sulfite, and sodium sulfite/EDTA did not prevent oxidative degradation of APAP. However, it was observed that purging the testing vials with nitrogen reduced the oxidation rate but ultimately did not prevent oxidation of APAP.

Consequently, while not intending to be bound by theory, it is believed that IBU likely contributes to APAP oxidation through the acidic functionality of its carboxylic acid moiety. As discussed in more detail in Example 2 herein, the sodium salt form of IBU in pre-formulation K did not demonstrate the same amber and dark brown color changes observed for pre-formulations F, H, and J associated with APAP degradation. It is hypothesized that the sodium salt form of IBU may reduce the acidity of the carboxylic acid moiety (i.e. raises the pKa), which in turn leads to increased APAP stability.

Example 2

Stability of Sodium and/or Potassium Ibuprofen and APAP Solutions

It has been discovered that ionization of API's that are chemically incompatible with APAP can influence APAP degradation rates. Specifically, it has been discovered that certain levels of ionization of incompatible API's using alkali metal salt forms can reduce degradation of APAP in solution. For example, increased APAP stability is observed in solution when IBU is in salt form with an alkali metal salt, such as sodium (Na) and/or potassium (K). While not intending to be bound by theory, it is believed that the resulting stability of APAP may be due to the reduced acidity of the carboxylic acid moiety of the sodium or potassium salts of IBU.

As noted in Example 1, the combination of APAP and the sodium salt form of IBU in pre-formulation K did not demonstrate the same amber and dark brown color changes associated with APAP degradation observed for pre-formulations F, H, and J having APAP and the free acid form of IBU. FIGS. 4A and 4B are photographs of pre-formulation K stability studies. Specifically, FIG. 4A shows a pre-formulation K control showing different vials of free acid IBU (7.5 wt. %) and APAP (12.5 wt. %) in the presence of PEG-400 (80 wt. %) in water, with vial 1a being a control at room temperature. Vials 2a and 3a were tested under accelerated stability conditions of 40° C./75% relative humidity, with vial 2a being an $N_2$-blanketed control after 6 days, and vial 3a being a non-$N_2$-blanketed control after 6 days. As shown, the room temperature vial 1a only shows a faint but distinguishable color change after 6 days, suggesting the slow but perceptible degradation of APA. Under the accelerated stability conditions, vials 2a and 3a show significant discoloration characteristic of APAP degradation.

FIG. 4B is a photograph of a different set of vials of pre-formulation K (sodium IBU and APAP in PEG-400). Analogous to the vials shown in FIG. 4A, vial 1b is pre-formulation K at room temperature after 6 days, vial 2b is $N_2$-blanketed pre-formulation K after 6 days of accelerated stability conditions at 40° C./75% relative humidity, and vial 3b is non-$N_2$-blanketed pre-formulation K after 6 days of accelerated stability conditions at 40° C./75% relative humidity. In contrast to the controls shown in FIG. 4A, the pre-formulation K remained clear for all three vials 1b-3b, with only a lightly pinkish tint after T=6 days of being stored at room temperature, $N_2$-blanketed at 40° C., and non-$N_2$-blanketed sample at 40° C., respectively.

The IBU in pre-formulation K was 100% ionized in the form of sodium IBU. Samples 1-3 in Table 4 below were prepared to explore the stability of APAP and IBU combinations in PEG-400 when IBU ionization is less than 100%, and when the salt form is potassium rather than sodium. As shown in Table 4, Sample 1 was prepared as an APAP/IBU/PEG-400 solution with an IBU ionization level of 40% in the form of potassium IBU. Sample 2 comprised 85% ionized potassium IBU/APAP/PEG-400, and Sample 3 comprised a pre-formulation K-based control of APAP/IBU/PEG-400 having sodium IBU dihydrate at a 100% ionization level.

Samples 1-3 were subjected to accelerated stability studies using the following procedures. Sample 1 was placed in a vial and placed on 40° C./75% relative humidity for 21 days. The solution turned a light amber by day 3 and deep brown/black after 21 days. Samples 2 and 3 were placed in vials and subjected to accelerated stability conditions of 60° C./60% relative humidity, and only displayed minor discoloration after 10 weeks (equivalent to 960 weeks of simulated room temperature conditions). Based on the fact that 40% ionization levels of potassium IBU slowly turned brown after 21 days under accelerated stability conditions (equivalent to 24 weeks of simulated room temperature conditions) and 85% ionization levels of potassium IBU showed almost no color changes after 10 weeks under accelerated stability conditions, it was concluded that (1) lower ionization levels down to at least 40% still displayed greatly improved stability properties compared to solutions with only free acid IBU (such as pre-formulations F, H, and J in Example 1); and (2) increasing the ionization levels to 85% and 100% resulting in even greater stability than 40% ionization levels. Additionally, both sodium and potassium salt forms of IBU displayed this stability.

TABLE 5-continued

65% IONIZATION OF POTASSIUM IBUPROFEN IN COMBINATION WITH APAP

| FORMULA 500 | SAMPLE 4 300 BATCH SIZE, g | SAMPLE 5 300 BATCH SIZE, g | SAMPLE 6 300 BATCH SIZE, g |
|---|---|---|---|
| PEG/DRUG RATIO | 1.2 | 1.2 | 1 |
| PVP % | 3.00 | 6.00 | 4.50 |
| PEG/DRUG | 1.200 | 1.200 | 1.000 |
| PEG & H20/DRUG | 1.39 | 1.39 | 1.19 |
| mg OF FILL/DOSE | 943.36 | 973.46 | 879.64 |

TABLE 4

DIFFERENT IONIZATION LEVELS OF IBU IN COMBINATION WITH APAP

| | SAMPLE 1 | | | SAMPLE 2 | | | SAMPLE 3 | | |
|---|---|---|---|---|---|---|---|---|---|
| FORMULA # | 1110.5 | mg/du | | 1120.78 | mg/du | | 1123.24 | mg/du | |
| mg WATER/DOSE | 88.8 | | | 85.0 | | | 85.0 | | |
| % IONIZATION | 40.0 | | | 85.0 | | | 100.0 | | |
| PEG/DRUG RATION | 1.366 | | | 1.600 | | | 1.463 | | |
| % PVP | 5.3 | | | 2.5 | | | 2.5 | | |
| INGREDIENT | GRAMS | % W/W | mg/DOSE | GRAMS | % W/W | mg/DOSE | GRAMS | % W/W | mg/DOSE |
| PEG 400 | 492.34 | 49.2335 | 546.74 | 1606.02 | 53.5340 | 600.00 | 1602.51 | 53.4172 | 600.00 |
| KOH | 14.69 | 1.4685 | 16.31 | 87.70 | 2.9233 | 32.76 | 0.00 | 0.0000 | 0.00 |
| DI WATER PURIFIED | 80.01 | 8.0004 | 88.84 | 227.52 | 7.5840 | 85.00 | 227.02 | 7.5674 | 85.00 |
| IBUPROFEN (Ibu) | 135.06 | 13.5059 | 149.98 | 334.59 | 11.1530 | 125.00 | 1.00 | 0.0000 | 0.00 |
| NaIbu DIHYDRATE | 0.00 | 0.0000 | 0.00 | 0.00 | 0.0000 | 0.00 | 427.75 | 14.2584 | 160.16 |
| APAP | 225.34 | 22.5338 | 250.24 | 669.17 | 22.3057 | 250.00 | 667.71 | 22.2571 | 250.00 |
| PVP K12 | 52.58 | 5.2579 | 58.39 | 75.00 | 2.5000 | 28.02 | 75.00 | 2.5000 | 28.08 |
| TOTAL | 1000.01 | 100.00 | 1110.50 | 3000.00 | 100.00 | 1120.78 | 2999.99 | 100.00 | 1123.24 |

Example 3

Stability of Sodium and/or Potassium Ibuprofen and APAP Solutions

Given the favorable stability profile observed for Samples 1-3 in Table 4 of Example 2, a new series of aqueous-based Samples 4-13 were prepared to investigate the stability of different IBU ionization levels of 45% ionization, 65% ionization, and 85% ionization, as well as to observe the effects of different amounts of excipients (such as PVP and PEG). Each of Samples 4-13 comprises approximately 125 mg of free acid IBU equivalent (as a mixture of free acid IBU and potassium IBU based on the ionization %) and 300 mg of APAP while varying the wt. % of PVP between 3.0-6.0 and the PEG/Drug ratio of 1.0-1.2.

Table 5 shows Samples 4-6 having 65% potassium IBU ionization levels and variations of PVP between 3.0-6.0 wt. % and a PEG/Drug ratio of 1.0-1.2.

TABLE 5

65% IONIZATION OF POTASSIUM IBUPROFEN IN COMBINATION WITH APAP

| FORMULA 500 | SAMPLE 4 300 BATCH SIZE, g | SAMPLE 5 300 BATCH SIZE, g | SAMPLE 6 300 BATCH SIZE, g |
|---|---|---|---|
| mg WATER/DOSE | 65 | 65 | 65 |
| % IONIZATION | 65 | 65 | 65 |

TABLE 5-continued

65% IONIZATION OF POTASSIUM IBUPROFEN IN COMBINATION WITH APAP

| FORMULA 500 | SAMPLE 4 300 BATCH SIZE, g | SAMPLE 5 300 BATCH SIZE, g | SAMPLE 6 300 BATCH SIZE, g |
|---|---|---|---|
| mg APAP/ml | 306.62 | 297.55 | 312.63 |
| ph | 6.88 | 7.29 | 7.33 |
| VISCOSITY, Pa s | 3.30 | 7.02 | 7.17 |
| DENSITY, g/ml | 1.16 | 1.16 | 1.16 |

Table 6 shows Samples 7-10 having 45% potassium IBU ionization levels and variations of PVP between 3.0-6.0 wt. % and a PEG/Drug ratio of 1.0-1.2.

TABLE 6

45% IONIZATION OF POTASSIUM IBUPROFEN IN COMBINATION WITH APAP

| FORMULA 500 | SAMPLE 7 300 BATCH SIZE, g | SAMPLE 8 300 BATCH SIZE, g | SAMPLE 9 500 BATCH SIZE, g | SAMPLE 10 500 BATCH SIZE, g |
|---|---|---|---|---|
| mg WATER/DOSE | 85 | 65 | 45 | 85 |
| % IONIZATION | 45 | 45 | 45 | 45 |
| PEG/DRUG RATIO | 1 | 1 | 1.2 | 1.2 |
| PVP % | 4.50 | 6.00 | 3.00 | 6.00 |
| % WATER | 9.52 | 7.34 | 4.92 | 8.62 |

TABLE 6-continued

| 45% IONIZATION OF POTASSIUM IBUPROFEN IN COMBINATION WITH APAP | | | | |
|---|---|---|---|---|
| FORMULA 500 | SAMPLE 7 300 BATCH SIZE, g | SAMPLE 8 300 BATCH SIZE, g | SAMPLE 9 500 BATCH SIZE, g | SAMPLE 10 500 BATCH SIZE, g |
| % WATER (REAL) | 10.07 | 7.90 | 5.46 | 9.11 |
| % PEG | 42.02 | 42.35 | 49.19 | 45.61 |
| PEG/DRUG | 1.000 | 1.000 | 1.200 | 1.200 |
| PEG & H20/DRUG | 1.24 | 1.19 | 1.33 | 1.44 |
| mg OF FILL/DOSE | 892.51 | 885.47 | 914.79 | 986.54 |
| mg APAP/ml | 322.88 | 326.41 | 313.19 | 278.75 |
| pH | 6.61 | 6.77 | 6.8 | 6.75 |
| VISCOSITY, Pa s | 2.57 | 7.64 | 4.03 | 3.74 |
| DENSITY, g/ml | 1.15 | 1.16 | 1.14600 | 1.15290 |

Table 7 shows Samples 7-10 having 45% potassium IBU ionization levels and variations of PVP between 3.0-4.5 wt. % and a PEG/Drug ratio of 1.0-1.2.

TABLE 7

| 85% IONIZATION OF POTASSIUM IBUPROFEN IN COMBINATION WITH APAP | | | |
|---|---|---|---|
| FORMULA 500 | SAMPLE 11 300 BATCH SIZE, g | SAMPLE 12 300 BATCH SIZE, g | SAMPLE 13 500 BATCH SIZE, g |
| mg WATER/DOSE | 85 | 65 | 85 |
| % IONIZATION | 85 | 85 | 85 |
| PEG/DRUG RATIO | 1 | 1 | 1.2 |
| PVP % | 4.50 | 3.00 | 3.00 |
| PEG/DRUG | 1.000 | 1.000 | 1.200 |
| PEG & H20/DRUG | 1.25 | 1.20 | 1.45 |
| mg OF FILL/DOSE | 908.65 | 873.98 | 971.92 |
| mg APAP/ml | 319.51 | 328.95 | 298.58 |
| pH | 7.79 | 7.80 | 7.75 |
| VISCOSITY, Pa s | 4.36 | 5.32 | 2.72 |
| DENSITY, g/ml | 1.16 | 1.16 | 1.16080 |

Each of Samples 4-13 was subjected to accelerated stability testing conditions of two weeks at 60% relative humidity and 60° C. and were analyzed for degradation and color changes characteristic of APAP degradation (as described, for instance, in Example 1). Of the three IBU ionization levels, Samples 4-6 (65% ionized IBU) were observed to have the least amount of APAP degradants using conventional HPLC assays, such as 4-aminophenol, with almost no discernable color change after two weeks under the accelerated stability conditions. Samples 11-13 (85% ionized IBU) displayed very faint, almost imperceptible color changes after two weeks under the accelerated stability conditions, with detectable APAP degradant (4-aminophenol) levels being very low in conventional HPLC assays. Finally, Samples 7-10 (45% ionized IBU) displayed a deeper discoloration compared to Samples 4-6 and 11-13, but APAP degradant levels were well within acceptable ranges according to conventional HPLC assay analysis.

In summary, the observation described in Example 2 that less than 100% ionized IBU can be used in combination with APAP was confirmed, with 85% ionization showing virtually no detectable APAP degradation, 65% ionization showing barely detectable APAP degradation, and 45% ionization showing minor degradation within acceptable ranges under accelerated stability conditions.

Example 4

Stability of Sodium and/or Potassium Naproxen and APAP Solutions

As previously discussed herein, the use of alkali metal salt forms to increase stability and chemical compatibility between incompatible API's is believed to not be limited to IBU-containing compositions, but is thought to be more broadly applicable to other API's having carboxylic acid functional groups or other similar acidic moieties. For example, naproxen is chemically incompatible with APAP, catalyzing the degradation of APAP in a similar manner observed for ibuprofen. For instance, FIG. 5 shows a photograph of two vials having an aqueous solution of 48.5% ionized sodium naproxen and acetaminophen in PEG-400, with one being at ambient temperature and humidity (vial 4a) after 7 days, and the other (vial 4b) under accelerated stability conditions of 40° C. and 75% humidity after 7 days. As shown, after 7 days, vial 4a has turned from a clear solution to an amber color, and vial 4b has turned from a clear solution to a dark brown color, both indicative of APAP degradation seen in aqueous solutions of IBU/APAP. While not intending to be bound by theory, it is believed that the carboxylic acid group of naproxen is catalyzing APAP degradation similarly to the mechanism seen with IBU/APAP. Thus, it is believed that an alkali metal salt forms of naproxen will similarly reduce the acidity of the naproxen carboxylic acid, which, in turn, will increase the stability of APAP when in solution with alkali metal naproxen salts.

The invention claimed is:

1. A composition comprising:

a first pharmaceutical ingredient comprising ibuprofen, dexibuprofen or naproxen, wherein 40%-100% of the first pharmaceutical ingredient is an alkali metal salt of ibuprofen, dexibuprofen or naproxen; and a second pharmaceutical ingredient comprising acetaminophen, wherein the second pharmaceutical ingredient is chemically incompatible with the first pharmaceutical ingredient, and the composition is an aqueous solution.

2. The composition of claim 1, wherein the alkali metal is sodium, potassium, or a combination of both.

3. The composition of claim 1, wherein 40%-95% of the first active pharmaceutical ingredient is the alkali metal salt.

4. The composition of claim 3, wherein at least 40%-85% of the first active pharmaceutical ingredient is the alkali metal salt.

5. The composition of claim 2, wherein the balance of the first active pharmaceutical ingredient is non-ionized.

6. The composition of claim 1, wherein the first active pharmaceutical ingredient further comprises ketoprofen, fenoprofen, dexketoprofen, flurbiprofen, oxaprozin, loxoprofen, diflunisal, etodolac, indomethacin, ketorolac, oxaprozin, piroxicam, salsalate, salicylic acid, indomethacin, tolmetin, sulindac, etodolac, ketordolac, diclofenac, aceclofenac, bromfenac, pharmaceutically acceptable salts thereof, or any combination thereof.

7. The composition of claim 6, wherein the second active pharmaceutical ingredient further comprises phenylephrine, chlorpheniramine and dextromethorphan, cetirizine, pseudoephedrine, brompheniramine, guaifenesin, doxylamine, or any combination thereof.

8. The composition of claim 1, further comprising polyethylene glycol (PEG), methoxy-PEG (mPEG), derivatives thereof, and/or any combination thereof.

9. The composition of claim 8, wherein PEG is PEG-200 to 1500.

10. A softgel capsule comprising a fill comprising the composition of claim 1.

11. A softgel capsule comprising:

a composition comprising:

ibuprofen, wherein 85% of the ibuprofen is an alkali metal salt of ibuprofen; and acetaminophen, wherein the composition is an aqueous solution.

* * * * *